US012649025B2

(12) United States Patent
Plain

(10) Patent No.: US 12,649,025 B2
(45) Date of Patent: Jun. 9, 2026

(54) ANTI-CHOKING DEVICE

(71) Applicant: John Plain, Park Ridge, NJ (US)

(72) Inventor: John Plain, Park Ridge, NJ (US)

( * ) Notice: Subject to any disclaimer, the term of this patent is extended or adjusted under 35 U.S.C. 154(b) by 489 days.

(21) Appl. No.: 18/197,442

(22) Filed: May 15, 2023

(65) Prior Publication Data

US 2023/0372600 A1     Nov. 23, 2023

Related U.S. Application Data

(60) Provisional application No. 63/343,273, filed on May 18, 2022.

(51) Int. Cl.
*A61M 1/00* (2006.01)
(52) U.S. Cl.
CPC ............... *A61M 1/804* (2021.05); *A61M 1/76* (2021.05); *A61M 1/81* (2021.05)
(58) Field of Classification Search
CPC ............ A61M 1/65; A61M 1/67; A61M 1/76; A61M 1/80; A61M 1/804; A61M 1/81; A61M 1/815; A61M 1/82; A61M 16/0009; A61M 16/0012; A61M 2205/073; A61M 2210/065; A61M 2210/0625; A61B 17/50
See application file for complete search history.

(56) References Cited

U.S. PATENT DOCUMENTS

| | | | | |
|---|---|---|---|---|
| 6,443,154 B1 * | 9/2002 | Jalde | ..................... | A61M 16/20 |
| | | | | 128/205.12 |
| 2007/0186928 A1 * | 8/2007 | Be'Eri | .............. | A61M 16/0009 |
| | | | | 128/204.21 |
| 2012/0221010 A1 * | 8/2012 | DeLuca | ................. | A61B 17/24 |
| | | | | 606/106 |
| 2021/0330908 A1 * | 10/2021 | dos Santos | ....... | A61M 16/0012 |
| 2022/0008643 A1 * | 1/2022 | Carver | ................... | A61B 17/50 |

* cited by examiner

*Primary Examiner* — Katherine H Schwiker
(74) *Attorney, Agent, or Firm* — Meagher, Emanuel, Laks, Golberg & Liao, LLP

(57) ABSTRACT

In accordance with various embodiments of the disclosed subject matter, an anti-choking apparatus is provided comprising a substantially hollow body comprising a first large cross section body region connected to a second large cross section body region via a small cross section body region; a plurality of auxiliary tubes coupled at respective first ends to respective portions of the body between the first large cross section body region and the small cross section body region, each of the auxiliary tubes having second ends with fans mounted thereat and configured to urge air through the auxiliary tubes and substantially hollow body; and a mouth tube couped at a first end to the small cross section body region and having a second end configured for insertion into an airway of a choking victim; wherein an airflow through the small cross section body region induces a pressure gradient within the mouth tube such that a reduced air pressure at the second end of the mouth tube exerts a force upon an obstruction within the airway.

19 Claims, 3 Drawing Sheets

ANTI-CHOKING DEVICE

CROSS-REFERENCE TO RELATED APPLICATION

This application claims the benefit of provisional patent application Ser. No. 63/343,273 filed on May 18, 2022, entitled ANTI-CHOKING DEVICE, which provisional patent application is incorporated herein by reference in its entirety.

FIELD OF THE DISCLOSURE

The present disclosure generally relates to an anti-choking device.

BACKGROUND

Every year in the United States alone approximately 5,000 people die as a result of choking on food that has become lodged in their airway.

Prior to 1974 the preferred and probably sole method used to dislodge food trapped in airways was to slap the victim vigorously on the back hoping that this would free the food up and out of the airway. This was an extremely ineffective method and indeed often forced food deeper into the airway.

In 1974 the Heimlich maneuver came into being wherein the "rescuer" would stand behind the victim and clasp his hands together under the person's diaphragm while exerting a goodly amount of pressure in on the diaphragm. The Heimlich maneuver has saved many lives throughout the years, but it is far from 100% effective and critics of it claim this maneuver can sometimes damage internal organs due to the intense pressure that must often times be used to force trapped food up and out of the airway.

The Heimlich maneuver also requires training of personnel so as to administer it properly, though trained personnel are usually not available when and where choking events occur. Further, a smaller person, even if trained in the Heimlich maneuver might not be able to encircle the body of a much larger person with their arms, thus rendering the Heimlich maneuver useless is such an instance.

Improvements are desired.

SUMMARY OF THE INVENTION

Various deficiencies in the prior art are addressed below by an anti-choking system and apparatus generally comprising a substantially hollow body comprising a first large cross section body region connected to a second large cross section body region via a small cross section body region; a plurality of auxiliary tubes coupled at respective first ends to respective portions of the body between the first large cross section body region and the small cross section body region, each of the auxiliary tubes having second ends with fans mounted thereat and configured to urge air through the auxiliary tubes and substantially hollow body; and a mouth tube couped at a first end to the small cross section body region and having a second end configured for insertion into an airway of a choking victim; wherein an airflow through the small cross section body region induces a pressure gradient within the mouth tube such that a reduced air pressure at the second end of the mouth tube exerts a force upon an obstruction within the airway.

The apparatus may further comprise an auxiliary mouth tube having a smaller cross-sectional area than the mouth tube, the auxiliary mouth tube configured to be disposed between the mouth tube and the airway of the choking victim.

The apparatus may further comprise a plunger assembly disposed at the end of the first large cross section body region, configured to force additional air through the small cross section body region in response to being urged further into the body. A plurality of valves may be configured to controllably seal the auxiliary tubes and an end of the second large cross section body region; and a switch may be disposed proximate a boundary between the small cross section body region and the first large cross section body region, and positioned to be activated by full extension of the plunger assembly into the body; wherein the switch, when activated, causes the plurality of valves to seal the auxiliary tubes and an end of the second large cross section body region.

The plunger assembly, when urged away from the full extension position within the body, causes air to be drawn from the body such that a reduced pressure is imparted to the mouth tube.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
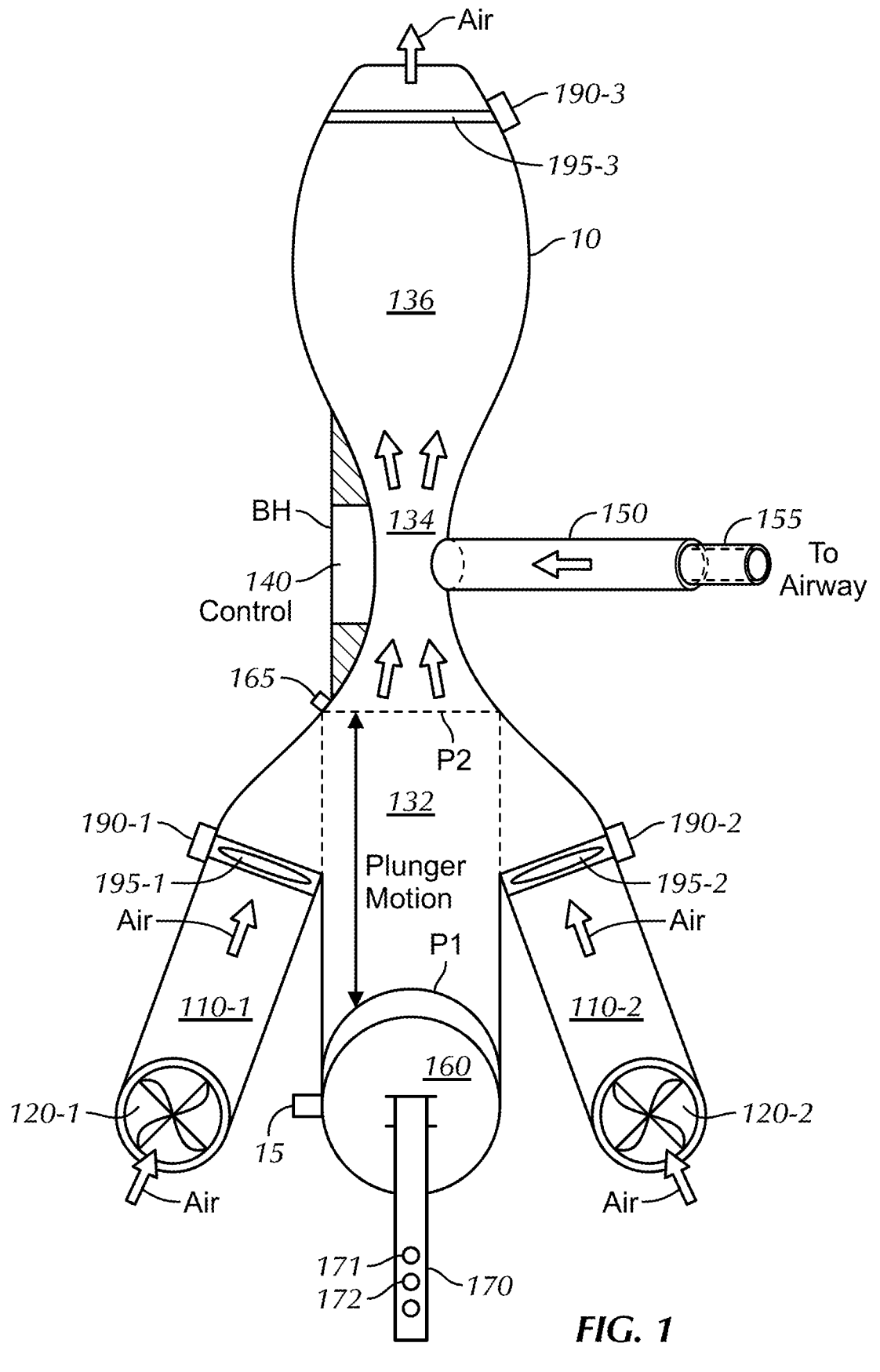
FIG. 1 depicts an anti-choking apparatus according to an embodiment.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for pedagogical purposes to aid the reader in understanding the principles of the invention and the concepts contributed by the inventor(s) to furthering the art and are to be construed as being without limitation to such specifically recited examples and conditions. Additionally, the term, "or" as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

Various embodiments provide a system and apparatus configured to enable rapid removal of an obstruction in a human airway. The embodiments use Bernoulli's principle in which a fluid flow when constrained to within certain fixed boundaries increases its velocity, such as when flowing from a region of greater cross-sectional area or dimension to a region of lesser cross-sectional area or dimension. The pressure in the region of greater cross-sectional area or dimension is greater than the pressure in the region of lesser cross-sectional area or dimension.

An apparatus according to the invention may comprise, illustratively, a cylindrical tube made out of clear plastic or other rigid material. This tube is of greater diameter or cross-sectional area at both the front and back portions of the tube and lesser diameter or cross-sectional area in the middle. A tube of this configuration may be denoted as a venturi tube with the narrow part in the middle being denoted as a venturi or venturi region.

Briefly stated, the operation of invention is as follows:

Air is forced to flow through the tube by fans placed near the front of the tube and as the air flows from the front of the tube through the venturi toward the back of the tube, a low-pressure region is created in the venturi, the narrow part of the tube.

A second tube also made of a rigid material is attached to the venturi tube such as in a direction that is perpendicular to the venturi tube. The second tube joins the venturi tube at the center of the venturi region and extends slightly into the venturi region though a small hole at the center of the venturi region.

It is assumed that the air pressure inside of a person's airway is atmospheric. When a person begins to choke, the venturi tube is held by the rescuer in a direction parallel to the person's mouth, illustratively with a front end of the venturi tube on the victims right and a back end on the victims left.

The second tube (with or without a mouthpiece or other adaptive apparatus) can now be placed inside of the victim's mouth and since the victim's mouth and airway are at atmospheric pressure and the venturi will be below atmospheric pressure, the ensuing pressure differential should force the trapped food to shoot out of the airway into the second tube and then into the low-pressure venturi, where it will be swept out of the back end of the venturi tube by the on-rushing air.

The purpose of the invention is to pull out food lodged in airways so as to avoid choking fatalities. In order to accomplish this, the inventive apparatus provides a suction sufficient to pull out the food or other obstruction.

The degree of suction provided depends on the difference in diameter between the wider ends of the venturi tube and the narrower in diameter venturi itself. I there must make this difference as great as realistically possible so as to plan for the worst-case scenario such as when a large piece of food is wedged tightly in the small airway of a child. The optimal design parameter for devices in accordance with the invention may be empirically determined, such as to provide effective removal of obstacles from people of different ages, sizes, and so on (e.g., children, adults, men, women, large people, smaller people, etc.).

FIG. 1 depicts an anti-choking apparatus according to an embodiment. The apparatus 100 is configured to create sufficient suction or vacuum force at a mouth tube 150 configured to be placed directly in the mouth or down the throat of a choking victim, or connected to a mouthpiece (not shown) or other adaptor, so as to enable an efficient application of the suction/vacuum generated by the anti-choking device such that food or other object lodged within the throat of a choking victim may be removed.

The apparatus 100 in a first embodiment comprises a substantially hollow body 10 comprising a first large cross section body region 132 connected to a second large cross section body region 136 via a small cross section body region 134 (i.e., a venturi region), the small cross section body region 134 pneumatically communicating with the mouth tube 150.

As depicted in FIG. 1, the first large cross section body region 132 is located at a proximate end of the hollow body 10, the second large cross section body region 136 is located at a distal end of the hollow body 10, and the small cross section body region 134 is located therebetween.

As depicted in FIG. 1, the substantially hollow body 10 further comprises a plurality (illustratively two) auxiliary tubes 110-1 and 110-2 formed therein and/or coupled to the hollow body 10 at a location between the proximate end of the body 10 and the small cross section body region 134, illustratively at a midway region of the first large cross section body region 132. Each of the auxiliary tubes 110-1 and 110-2 includes therein a respective fan 120-1 and 120-2, which fans 120 are configured to pull air in through the open ends of the tubes 110 and urge that air toward the first large cross section body region 132 of the body 10. The air being thus urged passes through the second large cross section body region 136 at an initial velocity v1 and passes through the small cross section body region 134 at an increased velocity v2 prior to being expelled through the open end of the second large cross section body region 136.

The air passing through the small cross section body region 134 at the increased velocity v2 results in a pressure differential between the air flowing in the small cross section body region 134 and the air in the mouth tube 150, thereby creating a pressure gradient or partial vacuum with respect to the mouth tube 150, which pressure gradient or partial vacuum when exerted or applied via a mouthpiece connected to the mouth tube 150 to an obstruction in a choking victim's throat will tend to pull the obstruction up the victim's throat and into the victim's mouth, from where the obstruction can be spit out.

The volume of air passing through the small cross section body region 134 is substantially the same as the volume of air passing through the first large cross section body region 132 (e.g., air urged therethrough via the auxiliary tube 110 fans 120). As such, the velocity v2 of air passing through the small cross section body region 134 is related to the relative cross-sectional area of the small cross section body region 134 and the first large cross section body region 132. The larger the cross-sectional area difference, the larger the velocity v2 of air passing through the small cross section body region 134.

The pressure gradient or partial vacuum created within the mouth tube 150 is related to the velocity v2 of air passing through the small cross section body region 134. The greater the velocity v2 of air passing through the small cross section body region 134, the greater the pressure gradient introduced to the mouth tube 150.

Further, the exertive force potential of the pressure gradient introduced to the mouth tube 150 is related to the volume of air within the mouth tube 150, wherein a pressure gradient exerted upon a larger volume mouth tube 150 will provide more of a vacuum force for removing a throat obstruction than the same pressure gradient exerted upon a smaller volume mouth tube 150. As discussed below, in some embodiments a smaller diameter (i.e., smaller volume) auxiliary mouth tube 155 may be attached to the mouth tube 150 if desired.

Generally speaking, air is forced down the body 10 by two fans placed in respective fan housings, one on each side of the venturi tube, and there is an opening on the top of each fan housing to allow air to enter the housing. Attached to each fan housing there is an auxiliary tube with each auxiliary tube being ended where it meets its respective fan housing and with each auxiliary tube being smaller in diameter than the venturi tube. Air is forced into the auxiliary tubes by the fans and each auxiliary tube is connected to the venturi tube, one on its right side and the other on its left side. The auxiliary tubes 110 may be positioned to closely parallel the body 10 so that when air leaves the auxiliary tubes 110 to enter the body 10, the majority of the air will be flowing straight down the body 10 and then through the venturi region 134 of the body 10. The components of air flow in the auxiliary tubes 110 entering the body 10 normal to the body 10 will substantially cancel each other out since they are substantially equal and opposite.

As depicted in FIG. 1, the proximate end of the hollow body 10 is sealed by a plunger assembly comprising a disk 160 and handle 170, the disk 160 configured to seal the proximate end of the first large cross section body region 132 and slideably engaged with inner surface of the first large cross section body region 132 such that manual operation of a plunger assembly handle 170 affixed to the plunger assembly disk 160 may cause the disk 160 to move between a first position P1 and a second position P2 so as to reduce the volume of the first large cross section body region 132, which action increases the velocity of air through the venturi region 134 of the body 10.

Figure 3:
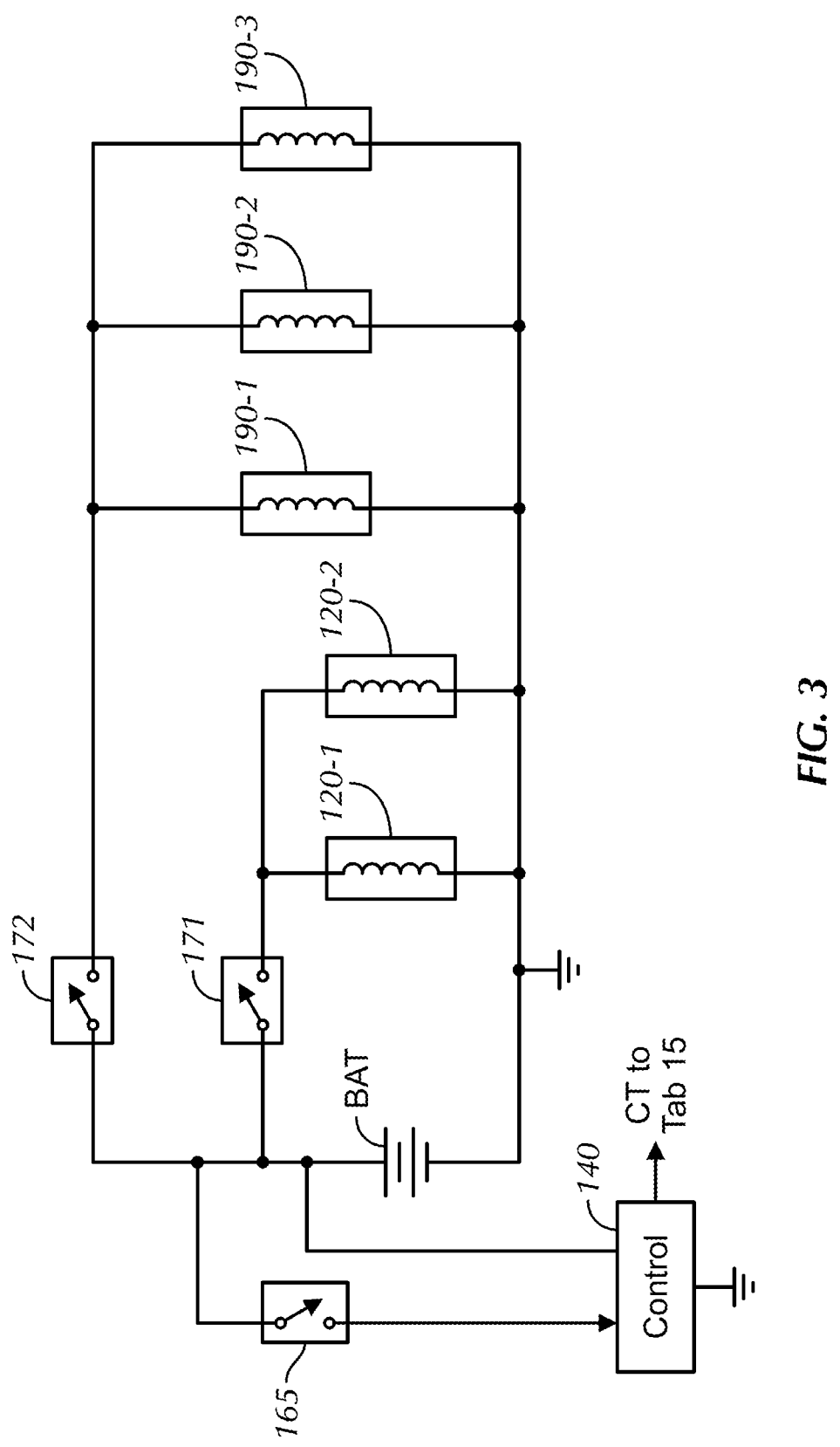
FIG. 3 depicts a simplified circuit diagram of the apparatus of FIG. 1.

As depicted in FIG. 1, the handle 170 of the plunger assembly 160, 170 includes thereon a first activation switch or button 171. The first switch 171, when activated, electrically connects a power source such as a battery BAT and related circuitry to the two (or more) fans 120, such as shown in FIG. 3. The first switch 171, when activated, places the apparatus 100 in a first mode of operation.

In the first mode of operation, activating the first switch 171 causes the fans 120 to begin operating, thereby pushing air into the hollow body 10 via the auxiliary tubes, past the small cross section body region 134, and out through the open distal end of the hollow body 10 (i.e., the open end of the second large cross section body region 136). In this mode of operation, the amount of vacuum force exerted upon a throat obstruction is primarily related to the pressure gradient or partial vacuum created within the mouth tube 150 is related to the velocity v2 of air passing through the small cross section body region 134.

As soon as the fans 120 are turned on, they begin forcing air through the venturi region 134, thus lowering the pressure in the venturi region 134. The choking victim's airway is assumed to be at the atmospheric pressure and if the venturi is small enough in diameter and then has low enough pressure it is hoped that the pressure differential between the airway and the venturi will be great enough to suck the food out of the airway with nothing more required.

If the obstruction is not removed, then the user of the apparatus 100 may apply additional force to assist in the removal of the obstruction via the plunger assembly 160, 170. Specifically, by manually manipulating the handle 170 the user may push the plunger assembly 160, 170 in and out of the body 10. In various embodiments, the diameter of the disk 160 is such that manual operation of the handle 170 may force the disk 160 through the first large cross section body region 132 toward a point within the body 10 where the smaller or venturi portion 134 of the body 10 begins. Pushing the plunger assembly 160, 170 manually down the body 10 creates a greater on rush of air into the venturi region 134 than that provided by the fans 120, with a corresponding increase in pressure gradient in the mouth tube 150 so as to increase suction force applied to the obstacle in the victim's airway.

FIG. 1 also depicts various options and alternate embodiments.

As depicted in FIG. 1, one optional embodiment contemplates that the two auxiliary tubes 110-1, 110-2 may be controllably sealed via respective optional valves 195-1, 195-2 configured to be controllably opened or closed via activation of respective optional solenoids 190-1, 190-2. Also depicted in FIG. 1 is an optional third solenoid 190-3 configured to controllably open or close an optional third valve 195-3 within, and preferably located towards the end of, the second large cross section body region 136 so as to controllably seal the end of the second large cross section body region 136. That is, each of the valves 195 is mechanically urged into an open position via a respective valve spring, and into a closed position via operation of a respective solenoid 190. It is noted that the depicted valves 195 comprise butterfly valves, though other types of valves and valving configurations may be used.

As depicted in FIG. 1, the handle 170 of the plunger assembly 160, 170 further includes an optional second activation switch or button 172. The second switch 172, when activated, electrically connects a power source such as a battery BAT to the two, three, or more solenoids 190, such as shown in FIG. 3. The second switch 172, when activated, places the apparatus 100 in a second mode of operation.

In the second mode of operation, such as might be employed after the first mode of operation does not yield the desired result of removing an obstruction, activating the second switch 172 causes the solenoids 190 to be energized (i.e., holding open the valves 195) until the plunger assembly 160, 160 is manually pushed into the body 10 until it touches/activates a switch 165 positioned at the entrance to the venturi region 134, at which time the solenoids 190 are deactivated and the valve springs of the valves 195 operate to shut the valves and seal the auxiliary tubes 110 and the end of the second large cross section body region 136.

In the second mode of operation, if the user manually and rapidly pushes forwards on the plunger assembly 160, 170 it will push additional air through the venturi region 134 of the body 10 and, as a result, increase the pressure gradient thereat. When the plunger assembly 160, 160 is pushed into the body 10 to the point where it touches and activates the switch 165 positioned at the entrance to the venturi region 134, the three (illustratively) solenoids 190 will be deactivated, thereby allowing the valve springs to close the valves 195 and seal the body 10.

If the user then manually and rapidly pulls backwards on the plunger assembly 160, 170, it will push air from the body 10 and, as a result, most of the air will be evacuated from the body 10 which creates additional suction force upon the airway obstacle via the mouth tube 155, 155.

Upon fully pulling back the plunger assembly 160, 170 such that the disk 160 comes to a stop at the front end of the body 10, most of the air has been pushed out of the front of the body 10 and the venturi region 134 of the body 10, leaving a partial vacuum extending from the entrance of the venturi region 134 to the plunger disk 160.

Optionally, when the switch 165 that closes the doors to the auxiliary tube valves 195-1, 195-2 and valve 195-3 at the back end of the body 10 is activated, as previously described, it also optionally causes a small solenoid-controlled tab 15 at the front entrance to the body 10 to be quickly lowered, thus preventing the disk 160 attached to the handle 170 from moving out of the venturi tube.

As a result of this significant difference in pressure through the venturi tube, the air in the back end of the venturi tube will very rapidly rush toward the front end of the venturi tube, thus creating an extremely rapid drop in pressure in the venturi itself, and given that the pressure in the choking victim's airway is atmospheric, there will be a very rapid change in the forces between the choking victim's airway and the venturi, and this in turn will cause a very rapid change in the acceleration of the trapped food which should jerk the trapped food right out of the airway as previously described when discussing the "jerk."

Thus, a very rapid change in the force on an object of small enough mass will create a very rapid change in the objects acceleration, meaning that the objects velocity will change very rapidly and hence the displacement of the object per unit time will increase very rapidly and therefore any food trapped in a victim's airway should be very quickly displaced out of the airway into the mouthpiece 150, 155 and then forced toward the front of the body 10 by the air rushing from the back of the body 10 toward the front of the body 10.

If the trapped food still has not been extricated from the person airway, the process just described can be repeated until the trapped food is "jerked" out of the airway.

In operation of my invention, the user should hold the mouthpiece so that it stays in the person' mouth with one hand, while holding the push rod with their other hand in order to push and pull it when and if necessary.

It should be noted that the handle 170 may be rotated upward and folded so that it lies on top of the body 10 for ease of storage in the charging sleeve.

As generally described above, the smaller or venturi portion 134 of the body 10 has attached to it a mouth tube 150, preferably at a right angle though other angles of attachment may be employed in various embodiments. The mouth tube 150 may be placed into the mouth of the person who is choking, preferably as close as possible to the airway of a person who is choking. Optionally attached to the end of the mouth tube 150 may be an auxiliary mouth tube 155, the auxiliary mouth tube 155 having a smaller diameter/cross sectional area than the mouth tube 150 and configured also to be inserted into the airway of the person choking.

In some embodiments, each of the fans 120 turns in an opposite direction, one clockwise and the other counter clockwise, with one fan being driving directly by an electric motor and the second fan driving by a mechanical coupling between the fans, such as via two gears wherein one gear is turning on the shaft of the motor driving fan and this one gear is meshed with another gear on the shaft of the second fan so as to drive that fan while reversing its direction of rotation.

As depicted in FIG. 1, control circuitry 140 includes a lithium-ion battery or batteries BAT within a control or battery housing BH for providing the necessary power and circuitry to operate the apparatus in its various modes. As depicted in FIG. 1, the battery housing BH is external to the air flow regions of the body 10, with the location being depicted on an external surface of the body 10 opposite from the mouth tube 150.

Figure 2:
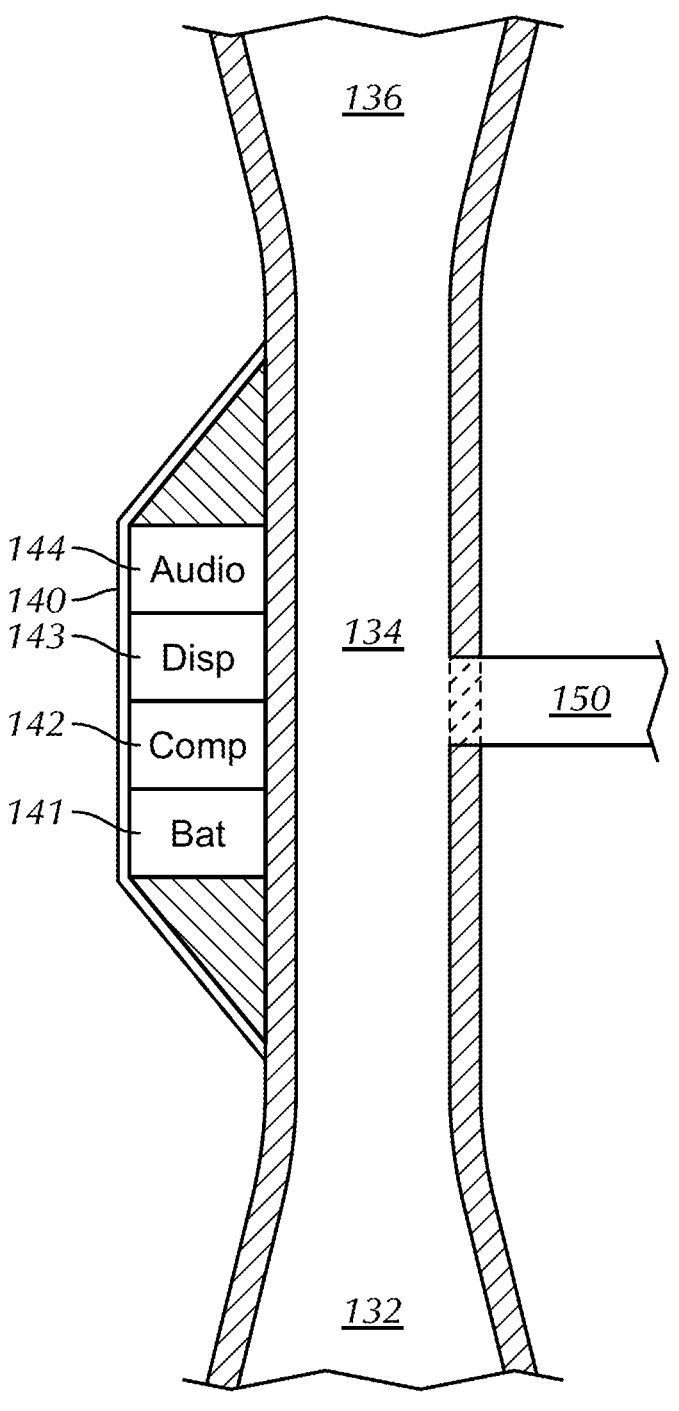
FIG. 2 depicts a detailed view of a portion of the apparatus of FIG. 1.

FIG. 2 depicts a detailed view of a portion of the apparatus of FIG. 1. Specifically, FIG. 2 depicts optional embodiments including, in addition to a battery 141 capable of operating the various solenoids as described above, a controller 140 includes a computing device 142, display device 143 and audio output device (speaker) 144 configured to present via visual or audio output user instructions, diagnostic information (e.g., battery charge level, mode of operation, etc.), and/or other information pertaining to the use and status of the apparatus 100.

The computing device and its related information display functions may be implemented in whole or in part by hardware or a combination of hardware and software via computing blocks or processing elements such as field programmable gate arrays (FPGAs) or similar, or via controllers including processor(s), tangible and non-transitory computer readable medium such as memory, input/output (I/O) circuitry and the like. That is, the functionality described herein with respect to the modes of operation, information presentation and so on may be provided via one or more computing devices 142 including a processor element (e.g., a central processing unit (CPU) and/or other suitable processor(s)), a memory (e.g., random access memory (RAM), read only memory (ROM), and the like), various cooperating modules/processes and various input/output devices or interfaces.

Thus, it will be appreciated that at least some of the functions depicted and described herein may be implemented one or more application specific integrated circuits (ASICs), FPGSs, and/or any other hardware equivalents. It is contemplated that some of the steps discussed herein may be implemented within hardware, for example, as circuitry that cooperates with the processor to perform various steps or functions as described herein. Portions of the functions/elements described herein may be implemented as a computer program product wherein computer instructions, when processed by a computing device, adapt the operation of the computing device such that the methods and/or techniques described herein are invoked or otherwise provided. Instructions for invoking the inventive methods may be stored in tangible and non-transitory computer readable medium such as fixed or removable media or memory, and/or stored within a memory within a computing device operating according to the instructions.

In an embodiment, displayed user the instructions may comprise some or all of the following:

Push red button (first switch 171) on handle to 170 to turn on fans 120 and activate the anti-choking apparatus.

Place mouth tube 150 into choking victim's mouth and place it as far down airway as possible to suction trapped food out.

If necessary, in the event that trapped food has not been suctioned into larger mouth tube, pull small tube 155 out from larger mouth tube and place it as far down airway as possible to suction trapped food out.

If trapped food is not suctioned away from airway within about 10 seconds, push green button (second switch 172) on handle 170, to begin the manual process described above using the plunger assembly 160, 170.

In various embodiments, the apparatus 100 may be stored in a "sleeve" with mounting brackets enabling it to be mounted on a wall where it is plugged into an electrical outlet or charging port to keep the battery BAT charged.

In various embodiments, the handle of the apparatus 100 protrudes from the storage sleeve and when the apparatus 100 is pulled out by the handle from this sleeve, a further switch is activated which immediately begins presenting audiovisual instructions to a user. These audiovisual instructions may be played in a repeating loop while the apparatus 100 is in use.

Further, the display 143 may be spring mounted to an outer surface of the body 10 such that is urged into a user display position.

FIG. 3 depicts a simplified circuit diagram of the apparatus of FIG. 1. Specifically, FIG. 3 depicts a battery BAT operatively coupled to each of the switches 171, 172, 173 discussed above. The first switch 171, when closed, provides power to a circuit including each of a plurality of fans 120, illustratively two fans 120-1 and 120-2 as discussed above. The second switch 172, when closed, provides power to a circuit including each of a plurality of solenoids 190, illustratively three valve solenoids 190-1 through 190-3 as discussed above.

FIG. 3 also depicts the battery BAT providing power to other portions of the control circuitry 140; namely, the computing device 142, display device 143 and audio output device (speaker driver) 144 as needed.

FIG. 3 also depicts a control signal CT generated by the controller 140 and used to control the tab 15 as previously discussed.

Various modifications may be made to the systems, methods, apparatus, mechanisms, techniques, and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof.

What is claimed is:

1. Apparatus for removing an obstruction from an airway, comprising:

a substantially hollow body comprising a first body region having a first cross-sectional area connected to a second body region having a second cross-sectional area via a third body region having a third cross-sectional area, wherein the first and second cross-sectional areas are larger than the third cross-sectional area;

a plurality of auxiliary tubes coupled at respective first ends to respective portions of the hollow body between the first body region and the third body region, each of the auxiliary tubes having second ends with respective fans mounted thereat and configured to urge air through the auxiliary tubes and the substantially hollow body in a first mode of operation; and a mouth tube coupled at a first end to the third body region and having a second end configured for insertion into an airway of a choking victim;

wherein an airflow through the third body region induces a pressure gradient within the mouth tube such that a reduced air pressure at the second end of the mouth tube exerts a force upon an obstruction within the airway.

2. The apparatus of claim 1, further comprising an auxiliary mouth tube configured to be disposed between the mouth tube and the airway of the choking victim, the auxiliary mouth tube having a cross-sectional area smaller than the third cross-sectional area.

3. The apparatus of claim 2, wherein the auxiliary mouth tube is stored within the mouth tube.

4. The apparatus of claim 1, further comprising:

a plunger assembly disposed at an end of the first body region, configured to force additional air through the third and second body regions in response to being urged further into the first body region in a second mode of operation.

5. The apparatus of claim 4, further comprising:

a plurality of valves configured to controllably seal the auxiliary tubes and a distal end of the second body region; and a plunger activated switch, disposed proximate a boundary between the third body region and the first body region, and positioned to be activated by full extension of the plunger assembly into the hollow body;

wherein the plunger activated switch, when activated, causes the plurality of valves to seal the auxiliary tubes and distal end of the second body region in a third mode of operation.

6. The apparatus of claim 5, wherein the plunger assembly, when urged away from the full extension position within the hollow body, causes air to be drawn from the hollow body such that a reduced pressure is imparted to the mouth tube.

7. The apparatus of claim 5, further comprising a controller configured for enabling activation of the plunger activated switch.

8. The apparatus of claim 7, further comprising a display device operatively coupled to the controller and configured thereby for displaying user instructions.

9. The apparatus of claim 8, wherein the display device operatively coupled to the controller is further configured thereby for displaying at least one of diagnostic information and apparatus status information.

10. The apparatus of claim 8, wherein the apparatus is configured to be stored within a storage sleeve, and a handle of the plunger assembly is configured to enable a user to remove the apparatus from the storage sleeve.

11. The apparatus of claim 10, further comprising a battery to supply power thereto, the battery being configured for charging via the storage sleeve.

12. The apparatus of claim 10, wherein the display device is spring mounted to an outer surface of the hollow body and urged thereby into a display position upon removal of the apparatus from the storage sleeve.

13. The apparatus of claim 10, wherein the controller configures the displaying of user instructions by the display device and causes the apparatus to enter the first mode of operation.

14. The apparatus of claim 13, further comprising an audio presentation device operatively coupled to the controller and configured thereby for presenting audible user instructions, wherein responsive to the display device being urged into the display position the controller configures the presentation of audible user instructions by the audio presentation device.

15. The apparatus of claim 14, wherein the user instructions include, after a predetermined time interval, user instructions for entering the second or third modes of operation.

16. The apparatus of claim 13, wherein the user instructions include, after a predetermined time interval, user instructions for entering the second or third modes of operation.

17. The apparatus of claim 7, further comprising an audio presentation device operatively coupled to the controller and configured thereby for presenting audible user instructions.

18. The apparatus of claim 17, wherein the audio presentation device operatively coupled to the controller is further configured thereby for presenting at least one of diagnostic information and apparatus status information.

19. The apparatus of claim 4, wherein each of the plurality of valves comprises a butterfly valve.

* * * * *